United States Patent
Moss

(10) Patent No.: US 9,998,237 B2
(45) Date of Patent: Jun. 12, 2018

(54) IMPLANT AND METHOD OF OPERATING THE IMPLANT

(71) Applicant: Biotronik SE & Co. KG, Berlin (DE)

(72) Inventor: Christian Moss, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 0 days. days.

(21) Appl. No.: 15/423,413

(22) Filed: Feb. 2, 2017

(65) Prior Publication Data

US 2017/0257174 A1 Sep. 7, 2017

(30) Foreign Application Priority Data

Mar. 7, 2016 (DE) .................. 10 2016 104 097

(51) Int. Cl.
*A61F 2/02* (2006.01)
*H04B 11/00* (2006.01)

(52) U.S. Cl.
CPC ............... *H04B 11/00* (2013.01); *A61F 2/02* (2013.01)

(58) Field of Classification Search
CPC ... H04B 11/00; A61F 2/02; A61B 5/00; A61B 5/0031
USPC .................................. 340/870.3; 607/60–61
See application file for complete search history.

(56) References Cited

U.S. PATENT DOCUMENTS

| | | | |
|---|---|---|---|
| 4,957,478 A | 9/1990 | Maniglia | |
| 5,735,280 A * | 4/1998 | Sherman | A61B 17/2202 600/1 |
| 7,024,248 B2 * | 4/2006 | Penner | A61B 5/00 128/903 |
| 7,283,874 B2 * | 10/2007 | Penner | A61B 5/0031 607/33 |
| 7,522,962 B1 | 4/2009 | Doron et al. | |
| 7,634,318 B2 * | 12/2009 | Tran | A61N 1/3787 607/61 |
| 8,277,441 B2 * | 10/2012 | Porat | A61K 9/0009 367/157 |
| 2002/0045921 A1 | 4/2002 | Wolinsky et al. | |
| 2008/0112885 A1 | 5/2008 | Okunev et al. | |

(Continued)

FOREIGN PATENT DOCUMENTS

DE 102012112237 A1 6/2014

OTHER PUBLICATIONS

European Search Report received from EP Application Serial No. 17153992.7, dated Jul. 12, 2017, 11 pages.

(Continued)

*Primary Examiner* — Albert K Wong
(74) *Attorney, Agent, or Firm* — ARC IP LAW, PC; Joseph J. Mayo

(57) ABSTRACT

Embodiments include an implant and a method of operating the implant. The implant includes a receiver that receives first ultrasound signals emitted by an external transmitting unit of a further apparatus. The receiver includes a piezo-element, which is excited by the first ultrasound signals at a first resonance frequency (f1) and therefrom converts the mechanical energy transferred with the first ultrasound signals into electrical energy. In embodiments of the invention, the piezoelement is additionally excited at a second resonance frequency (f2), which differs from the first resonance frequency (f1), and at the second resonance frequency (f2) operates as a transmitter to transmit second ultrasound signals.

12 Claims, 11 Drawing Sheets

(56) References Cited

U.S. PATENT DOCUMENTS

2010/0295419 A1 11/2010 Fujii
2011/0218594 A1 9/2011 Doron et al.
2012/0312456 A1 12/2012 McAlpine et al.
2014/0336474 A1 11/2014 Arbabian et al.
2014/0350248 A1 11/2014 Ren et al.

OTHER PUBLICATIONS

European Search Report received from EP Application Serial No. DE102016104097.5, dated Feb. 17, 2017, 7 pages.

\* cited by examiner

IMPLANT AND METHOD OF OPERATING THE IMPLANT

This application claims the benefit of German Patent Application DE 10 2016 104 097.5, filed on 7 Mar. 2016, the specification of which is hereby incorporated herein by reference.

BACKGROUND OF THE INVENTION

Field of the Invention

Embodiments of the invention generally relate to a medical implant and a method of operating the medical implant.

Description of the Related Art

Generally, medical endoprostheses or implants for a wide range of applications have been typically used in a large variety. Generally, implants are divided into passive and active implants. Passive implants typically tend to perform mechanical tasks in the body into which they are inserted. Passive implants are typically, for example, a stent, a replacement heart valve, a breast implant, prosthetic body limbs, or optical lenses. By contrast, generally, active implants contain an electronics unit and are able to detect specific body states or perform a treatment. Examples of active implants generally include cardiac pacemakers, neurostimulators, drug delivery pumps, or defibrillators. Typically, further applications of active implants also include sensors for body functions, for example pressure sensors as described in United States Patent Application 20020045921, to Wolinskey et al., entitled "Implantable Pressure Sensors and Methods for Making and Using Them". Embodiments of the present invention generally relate to active implants in accordance with the above distinction, as will be further discussed below.

Generally, when using active implants, it may be necessary to exchange data relating to the control of the implant or generated by the implant, for example measurement data of a sensor integrated into the implant, with a unit that is external in relation to the implant. Typically, such a unit that is external in relation to the implant can be, for example, a unit outside the body, such as a programming apparatus or a further implant. In order to simplify the presentation, generally, a unit of the type above that is outside the body, or a further implant, will be referred to hereinafter as a further apparatus. Typically, it is desirable that a data exchange with the further apparatus is performed wirelessly. In addition, generally, the implants should be as small as possible so as to load the body to a minimal extent on account of their spatial requirement.

Typically, primarily galvanic communication/impedance modulation-based communication, inductive near-field telemetry systems or radio systems are used for data transfer between the implant and an apparatus that is outside the body for data capture and/or data processing. Typical systems, however, have a series of disadvantages. In the case of galvanic communication/impedance modulation-based communication, generally, housing feedthroughs or electrodes are necessary on the outside of the housing. In addition, typically, electrodes have to be affixed to the body surface on the side of the apparatus outside the body, which is practical only to a limited extent with frequent use of the interface. Generally, inductive near-field telemetry has a heavily limited transfer radius, in particular in the case of miniaturisation of implants and the associated use of small coils. With regard to radio data transfer, typically, there is the known disadvantage that the antenna must be of a certain size, which prevents further miniaturisation. In addition, generally, it is not possible to place the antenna in a housing made of conductive material, such as titanium, and therefore the integration of an antenna into an implant is associated with greater outlay. Typically, a further known disadvantage in the case of radio data transfer lies in the fact that the energy requirement for the data transfer rises depending on the depth of implantation of the implant in the body. Generally, this inevitably leads to the use of larger energy sources, which is also contrary to further miniaturisation.

Typically, ultrasound has also been used for the exchange of data with an implant. Generally, the systems proposed previously, however, are technically complex and take up a large amount of space. For example, the use of ultrasound for data transfer are described in the publication entitled "Deeply implanted medical device based on a novel ultrasonic telemetry technology", thesis no. 5730 (2013) at the École Polytechnique Fédérale de Lausanne (Swiss Federal Institute of Technology in Lausanne) by M. Peisino, in U.S. Pat. No. 5,861,018, to Feierbach, entitled "Ultrasound Transdermal Communication System and Method", in United States Patent Application Publication 20100249882, to Houben, entitled "Acoustic Telemetry System for Communication with an Implantable Medical Device", and in United States Patent Application Publication 20020045921, to Wolinsky et al., entitled "Implantable Pressure Sensors and Methods for Making and Using Them". The implants according to the prior art patents and publications generally have a piezoelement, with which ultrasound signals sent by an external transmission unit can be received and converted into electrical signals.

For example, U.S. Pat. No. 6,140,740, to Porat et al., entitled "Piezoelectric Transducer" generally describes a passive method for ultrasound communication in which a sound wave originating from an external transmitter is modulated in the reflection. According to Porat et al., the patient apparatus necessary for the method, and the production of the sound converter, however, are very complex.

In view of the above, there is a need of an implant having the possibility for wireless data transfer, which is of a simple structure and allows for a further miniaturisation.

BRIEF SUMMARY OF THE INVENTION

One or more embodiments of the invention include an implant with various features as will be discussed below and as presented in the claims. In at least one embodiment, the implant may include a receiver in the form of or such as a piezoelement that receives first ultrasound signals sent from a transmission unit of a further apparatus such as a second device. In one or more embodiments, the receiver may be excited at a first resonance frequency by the first ultrasound signals and may convert the mechanical energy transferred with the first ultrasound signals into electrical energy. In at least one embodiment, the piezoelement may be excited at a second resonance frequency, wherein the second resonance frequency differs from the first resonance frequency. In one or more embodiments, the piezoelement, at the second resonance frequency, may be operated as or may be or may include a transmitter to transmit second ultrasound signals.

According to at least one embodiment of the invention, the piezoelement may be used to receive the first ultrasound signals and to transmit the second ultrasound signals and therefore may operate as, or may be or may include a transceiver. As such, by way of one or more embodiments, a low technical outlay may be necessary to transmit the first ultrasound signals and to receive the second ultrasound signals. In at least one embodiment, when transmitting and receiving the ultrasound signals, the piezoelement operates in or includes a resonance mode, such that an effective energy conversion may occur. For operation in the resonance mode, according to one or more embodiments, both series resonance frequency and parallel resonance frequency may be used as resonance frequency when transmitting and when receiving. In at least one embodiment, regarding energy efficiency, the series resonance frequency may be used when transmitting and when receiving the ultrasound signals.

In one or more embodiments, as a result of the conversion of the received first ultrasound signals, the piezoelement generates sufficient electrical energy to generate and send second ultrasound signals at the second resonance frequency. In at least one embodiment of the invention, a passive communication method may be provided for the active implant, wherein the electrical energy converted from the first ultrasound signals may be used to excite the piezoelement to vibrate at the second resonance frequency, and wherein the piezoelement delivers ultrasound which may be received via a further apparatus. According to one or more embodiments of the invention, the implant may operate without an additional energy source. As such, at least one embodiment includes a significant saving of space and corresponding miniaturisation of the implant. In one or more embodiments of the invention, the implant may operate with an energy source. As such, in at least one embodiment, energy saving may be obtained with the implant, such as during frequently communicating applications, wherein a significant extension of the service life of the implant and/or reduction of the overall size of the energy source of the implant and therefore a reduction of the overall size of the implant may be achieved.

In one or more embodiments, in conjunction with the transmission of ultrasound signals, the implant may include a metal housing.

At least one embodiment of the invention, compared to non-ultrasound-based data transfer methods, includes significant advantage as a result of an improved possibility of integration and miniaturisation, as discussed herein. In one or more embodiments, sound converters such as piezoelements may be integrated into hermetically sealed and militarised housings of the implant.

According to at least one embodiment of the invention, the implant may include two or more implants, wherein communication may be provided between the two or more implants in a network. In one or more embodiments, for example, a first implant may be used as a further apparatus, wherein the further apparatus may include one or more of an ultrasound transmitter, an ultrasound receiver, a data processor that processes data and a storage device, and wherein the first implant may include a small energy store, for example a small battery. At least one embodiment of the invention may include a second implant, the structure of which will be described below in detail, which communicates passively. In one or more embodiments, the implant may be used when there is only very little space available in order to introduce the implant, for example at a specific measurement point for a body parameter. In at least one embodiment, the implant may be a node in a network of implants that communicate with one another or in a network of external apparatuses and implants.

In one or more embodiments of the invention, the piezoelement may be excited simultaneously at the first resonance frequency and the second resonance frequency. As a result, in at least one embodiment, the device may operate at a faster speed.

In at least one embodiment, the piezoelement may be formed as or may include a thin rectangular piezoelectric layer, such as a layer with a height H that may range from 100 μm to 1000 μm, such as ranging from 250 μm to 350 μm. In one or more embodiments, the thin rectangular piezoelectric layer may include side edges with lengths L and B, wherein the lengths L, B of the side edges may determine the first and second resonance frequencies. In at least one embodiment, the direction in which the height H of the piezoelectric layer is measured may run perpendicularly to the side edges L, B. In one or more embodiments, the required and/or desired resonance frequencies may be easily adjusted by the lengths L, B of the side edges. In at least one embodiment, the thin rectangular piezoelectric layer may include lead zirconate titanate (PZT).

In one or more embodiments of the invention, the piezoelement may include a total of at least two electrodes, each formed in a layer-like manner, wherein a first electrode is arranged on an underside of the thin rectangular piezoelectric layer and at least one second electrode is arranged on an upper side of the thin rectangular piezoelectric layer. In at least one embodiment, the upper side of the piezoelectric layer may include a side face having the greatest extent of the piezoelectric layer and the underside is the side of the piezoelectric layer opposite the upper side.

In one or more embodiments of the invention, the piezoelement may include a total of at least three electrodes, each formed in a layer-like manner, wherein a first electrode is arranged on the underside of the thin rectangular piezoelectric layer, and a second electrode and at least one third electrode, which may be galvanically separated from the second electrode, may be arranged on the upper side of the thin rectangular piezoelectric layer.

In at least one embodiment, the second electrode and the at least one third electrode may be arranged on the upper side of the piezoelectric layer adjacently, for example as a rectangular layer.

According to one or more embodiments of the invention, the electrodes arranged on the upper side may include ribs formed in a comb-like manner, wherein the ribs of the second electrode and the ribs of the third electrode engage with one another. For example, in at least one embodiment, each rib of the second electrode lies in a gap between two ribs of the third electrode, and vice versa.

By way of at least one embodiment, the second electrode and the third electrode are on the upper side of the piezoelectric layer, such that the complexity of the circuitry is simplified during the simultaneous transmitting and receiving operation or mode at a number of frequencies. In one or more embodiments, there may be no galvanic contact between the second electrode and the third electrode on the upper side of the piezoelectric layer, wherein both electrodes are electrically insulated from one another. Thus, in at least one embodiment, any additional separation between the electrodes is not needed.

One or more embodiments of the invention may include an amplifier, wherein the input of the amplifier is connected to an energy supply, which is connected via a rectifier to the piezoelement. In at least one embodiment, with the aid of the electrical energy converted at the first resonance frequency by the piezoelement, the amplifier may generate an electrical output signal (an AC voltage), wherein the piezoelement may be excited at the second resonance frequency via the amplifier and may generate the corresponding second ultrasonic signal to be sent. By way of one or more embodiments, the amplifier may be or may include a class E amplifier.

At least one embodiment may include a single electrode on the upper side of the piezoelectric layer and a single electrode on the underside of the piezoelectric layer, wherein the electrodes on the upper side and underside of the piezoelement may be short-circuited by the class E amplifier, which may be remedied by a circulator or a diplexer. As such, in at least one embodiment, with the structuring of the electrodes on the upper side of the piezoelectric layer, such a separation and therefore the associated circuitry outlay may be avoided.

In order to attain a good separation of the excitation of the piezoelement in the transmitting and receiving mode, according to one or more embodiments, the length L, B of the side edges of the piezoelectric layer may be selected such that the frequency spacing between the first resonance frequency and the second resonance frequency is at least 100 kHz. In one or more embodiments the length L, B of the side edges of the piezoelectric layer may be selected such that the frequency spacing between the first resonance frequency and the second resonance frequency is at least 450 kHz.

In order to provide a transfer of data from the implant to a further apparatus, at least one embodiment may include an external receiver or a further implant, and the amplifier may include a modulator, such that the output signal to transfer the data may be modulated via the modulator. In one or more embodiments, various modulation methods, such as frequency, amplitude or phase modulation, may be used for this purpose.

At least one embodiment of the invention may include a method of operating the implant, wherein the piezoelement may be excited at the first resonance frequency and may receive the first ultrasound signals emitted by the transmitting unit of the further apparatus. In one or more embodiments, the piezoelement may be excited at the second resonance frequency via the generated electrical energy and may emit the second ultrasound signals. The method according to at least one embodiment of the invention has the advantages discussed above in conjunction with the implant. In one or more embodiments, an AC voltage may be generated as an output signal, such as via the amplifier with use of the electrical energy generated by the first ultrasound signals, and the AC voltage may be used to excite the piezoelement at the second resonance frequency.

In at least one embodiment, the modulator may modulate the electrical output signal of the amplifier.

With an appropriate modulation, by way of one or more embodiments, data may be transferred to the implant via the first ultrasound signal emitted to the implant. As such, in at least one embodiment, the implant may communicate bidirectionally with a further apparatus. With the described piezoelement, one or more embodiments may include a bidirectional communication of the implant in alternating operation (half-duplex) and in counter operation (full-duplex).

The implant according to at least one embodiment of the invention and the method according to at least one embodiment of the invention will be described hereinafter. By way of one or more embodiments, the features of the invention will be shown and described herein in conjunction with the drawings.

BRIEF DESCRIPTION OF THE DRAWINGS

The above and other aspects, features and advantages of at least one embodiment of the invention will be more apparent from the following more particular description thereof, presented in conjunction with the following drawings, wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
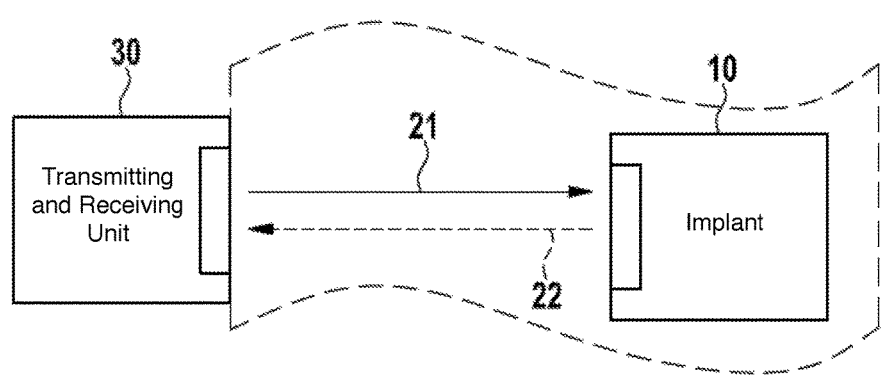
FIG. 1 schematically shows a first exemplary embodiment of an implant and an external transmitting and receiving unit in the form of a block diagram, according to one or more embodiments of the invention.
Figure 2:
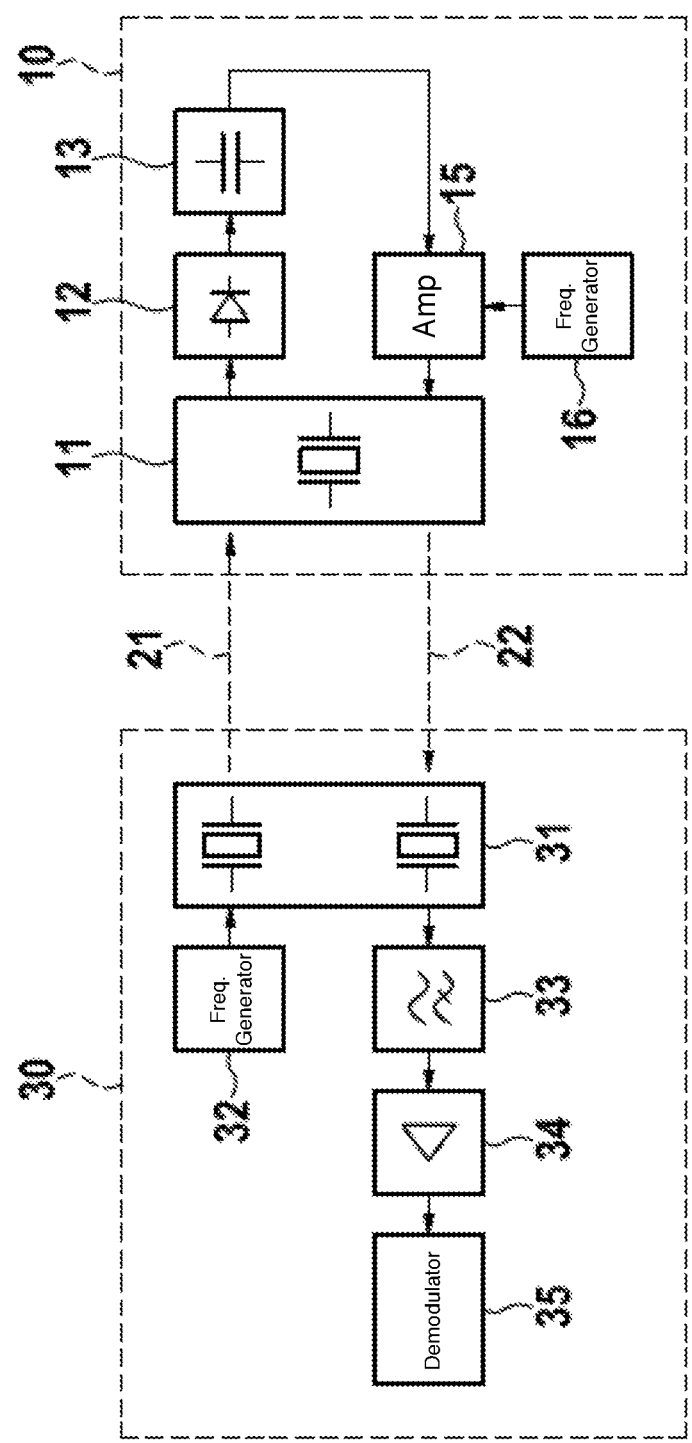
FIG. 2 schematically shows the implant and the transmitting and receiving unit of FIG. 1, in detail in the form of a block diagram, according to one or more embodiments of the invention.
Figure 3:
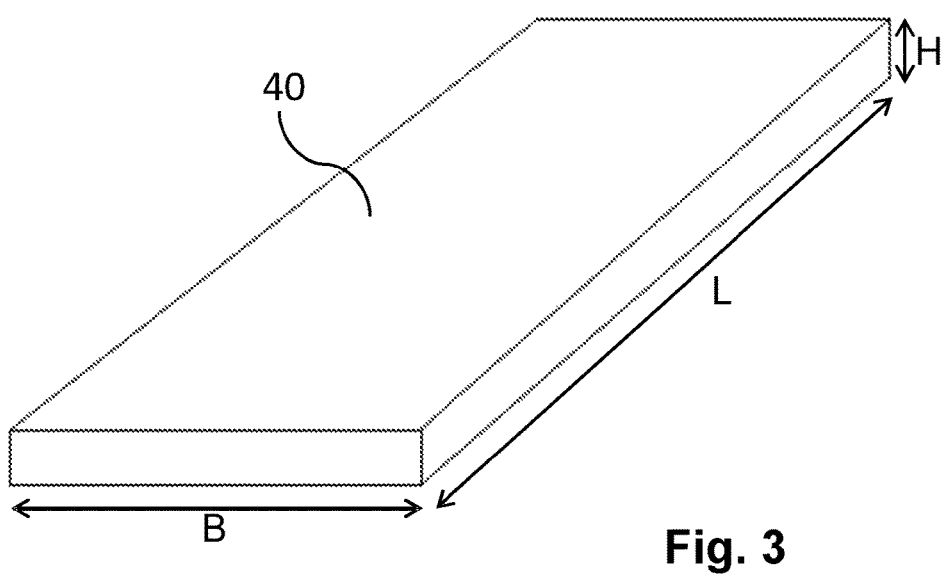
FIG. 3 schematically shows a piezoelectric layer in a perspective side view, according to one or more embodiments of the invention.

FIGS. 1 and 2 schematically show a system that includes an implant 10, and a transmitting and receiving unit 30 of a further apparatus (not shown), according to one or more embodiments of the invention. In at least one embodiment, the further apparatus may be or may include one or more of a programming apparatus, a patient apparatus, and a further implant. By way of one or more embodiments, first ultrasound signals 21 may be sent from the transmitting and receiving unit 30 of the further apparatus, wherein the first ultrasound signals 21 reach the implant 10 through the body and are received in the implant via the piezoelement 11. In at least one embodiment, the piezoelement 11, as will be described in greater detail further below, may serve as, may be or may include a transmitter to transmit second ultrasound signals 22 from the implant 10 to the transmitting and receiving unit 30 of the further apparatus to transfer data from the implant 10 to the further apparatus In one or more embodiments, the piezoelement 11 of the implant 10 may include a piezoelectric layer 40 that may be one or more of a planar, rectangular, and ceramic piezoelectric layer, as shown in FIG. 3. In at least one embodiment, the piezoelectric layer 40 may include a specific, predefined length L, a specific, predefined width B, and a specific, predefined height H. In one or more embodiments, the height H of the piezoelectric layer 40 may be smaller compared to the length L and the width B. In at least one embodiment, the height H may be 300 μm. As such, in one or more embodiments, the piezoelectric layer 40 is thin.

In at least one embodiment, resonance frequencies of the piezoelement 11 may be predefined by the length L and the width B of the piezoelectric layer 40. By exciting the piezoelectric layer 40 at the series resonance frequencies, in one or more embodiments, mechanical energy may be converted into electrical energy particularly efficiently, and vice versa.

Figure 4:
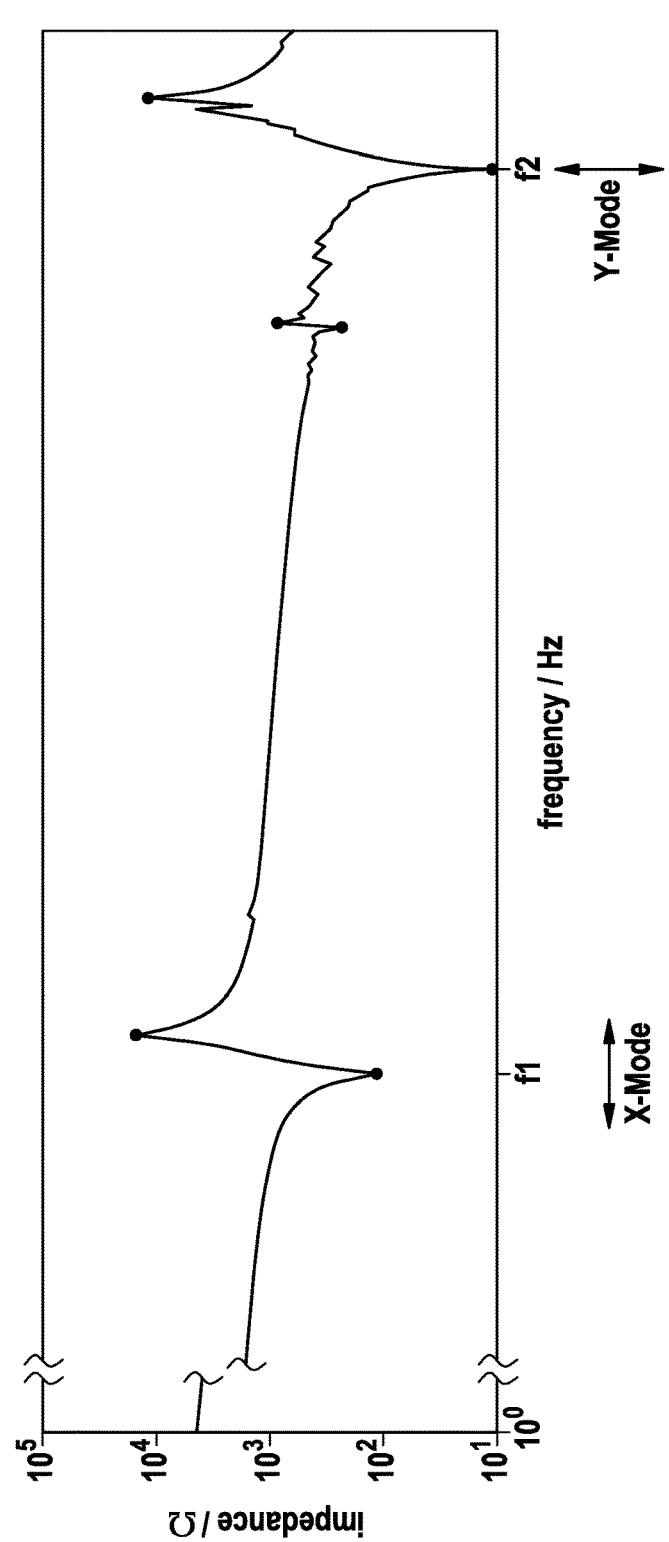
FIG. 4 schematically shows an impedance curve (dependent on frequency) of a piezoelement of the implant of FIG. 1, according to one or more embodiments of the invention.
Figure 5:
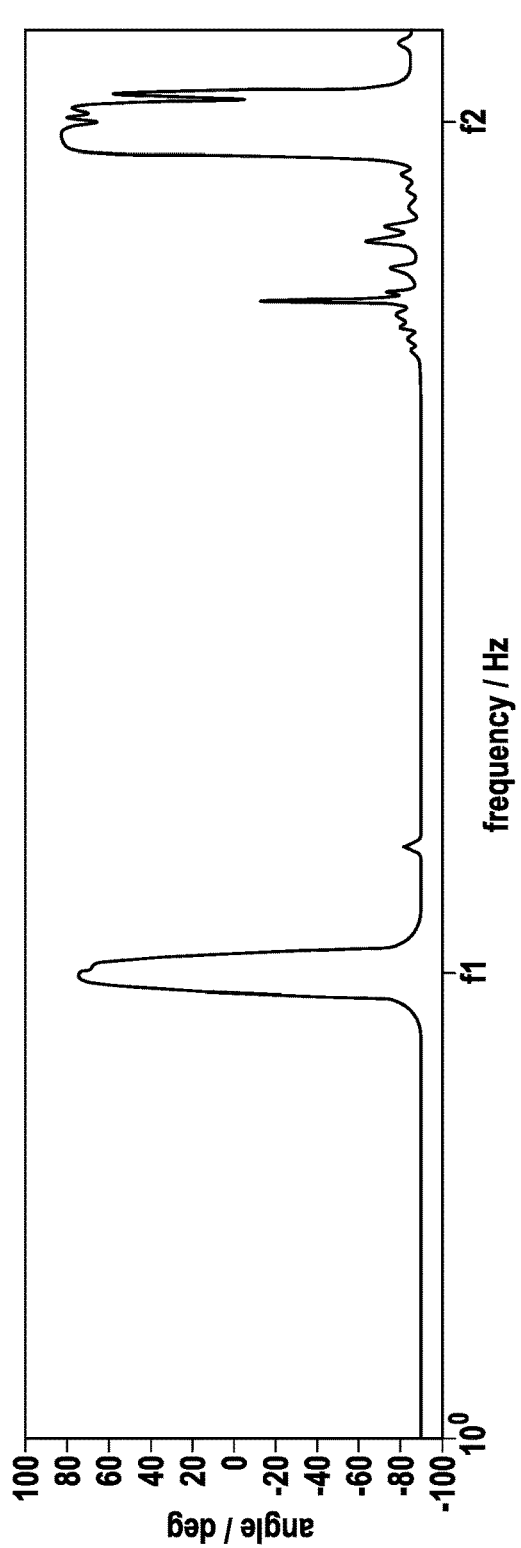
FIG. 5 shows a phase curve of a piezoelement of the implant of FIG. 1, according to one or more embodiments of the invention.

By way of at least one embodiment, the piezoelectric layer 40 may include a length L of 5 mm, a width B of 2 mm, and a height H of 300 μm and may include a lead zirconate titanate (PZT) material that includes a series resonance frequency of $f_1$=320 kHz (X-mode) and a series resonance frequency of $f_2$=800 kHz (Y-mode). In one or more embodiments, the curve of the absolute value of the impedance depending on the frequency of the piezoelectric layer 40 is shown in FIG. 4. Accordingly, by way of at least one embodiment, FIG. 5 shows the curve of the phase dependency between current and voltage on the frequency of the piezoelectric layer 40. In order to measure such curves, according to one or more embodiments, the piezoelectric layer 40 may be contacted on its upper side and underside, such that the electric field lines run from the upper side to the underside or from the underside to the upper side (in accordance with the polarity of the applied voltage) of the piezoelectric layer 40 and may be examined with the aid of an impedance analyser. In at least one embodiment, jumps in an impedance curve discussed above may each indicate a resonance at the corresponding frequency. In one or more embodiments, a local minimum in each case characterizes a series resonance frequency of the piezoelectric layer 40 such as the ceramic of the piezoelectric layer. In at least one embodiment, the subsequent local maximum characterizes the corresponding parallel resonance frequency.

Figure 6:
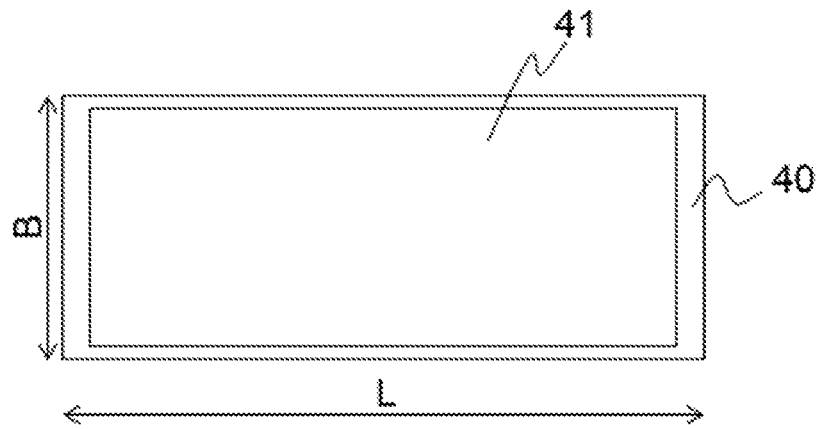
FIG. 6 schematically shows a first exemplary embodiment of a piezoelement of the implant in a view from below, according to one or more embodiments of the invention.
Figure 7:
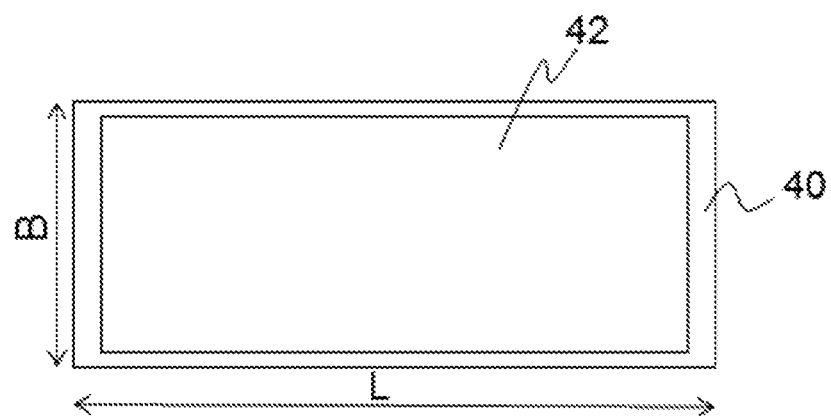
FIG. 7 schematically shows the piezoelement of FIG. 6 in a view from above, according to one or more embodiments of the invention.
Figure 8:
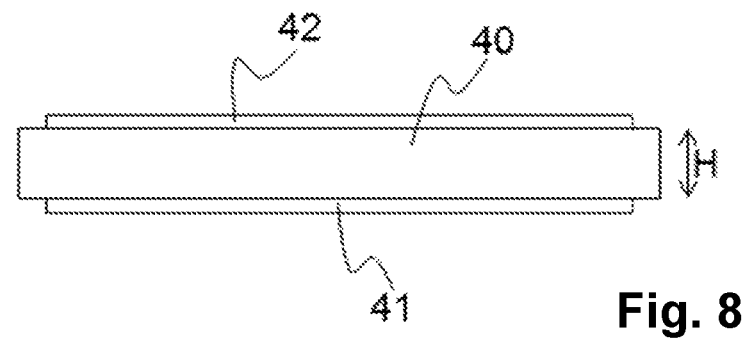
FIG. 8 schematically shows the piezoelement of FIG. 6 in a view from the side, according to one or more embodiments of the invention.

According to one or more embodiments, the piezoelectric layer 40 of the piezoelement 11, as shown in FIGS. 6 to 8, may include two layer-like electrodes, such as a first, layer-like electrode 41 on the underside, as shown in FIG. 6, and a second layer-like electrode 42 on the upper side, as shown in FIG. 7. In at least one embodiment, the upper side and the underside of the piezoelectric layer 40 may be opposite side faces having the greatest extent. In one or more embodiments, the electrodes 42, 41 may occupy the entire or almost the entire surface of the upper side and underside of the piezoelectric layer 40.

Figure 10:
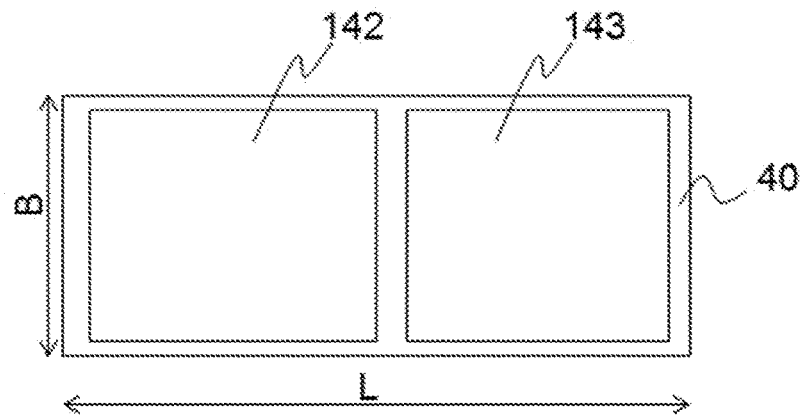
FIG. 10 schematically shows a second exemplary embodiment of a piezoelement of the implant in a view from above, according to one or more embodiments of the invention.
Figure 11:
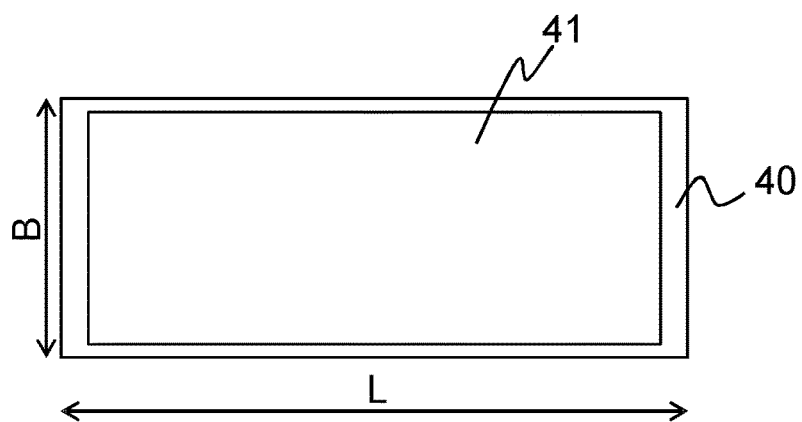
FIG. 11 schematically shows the piezoelement of FIG. 10 in a view from below, according to one or more embodiments of the invention.
Figure 12:
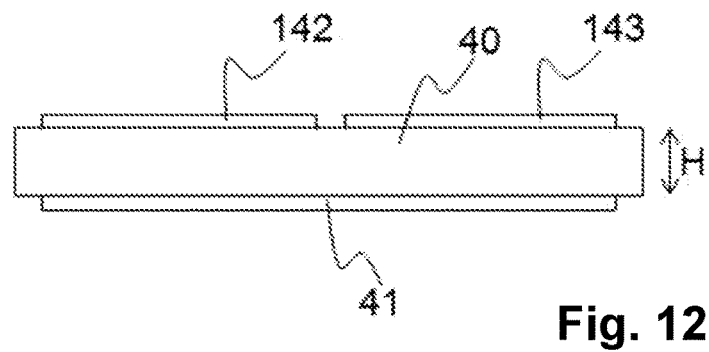
FIG. 12 schematically shows the piezoelement of FIG. 10 in a view from the side, according to one or more embodiments of the invention.

By way of at least one embodiment, the piezoelement 11 as shown in FIGS. 10 to 12, may include a second electrode 142 and a third electrode 143 in the form of two adjacently arranged layers on the upper side of the piezoelectric layer 40, as shown in FIG. 10. According to one or more embodiments, the piezoelement 11 may include a single first electrode 41 on the underside, as shown in FIG. 11. In at least one embodiment, the second electrode 142 and the third electrode 143 may be galvanically separated from one another.

Figure 14:
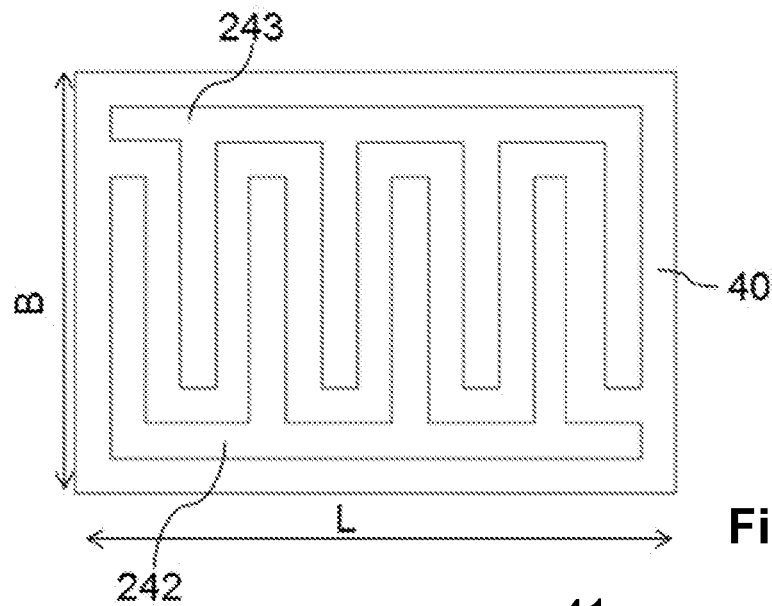
FIG. 14 schematically shows a third exemplary embodiment of a piezoelement of the implant in a view from above, according to one or more embodiments of the invention.
Figure 15:
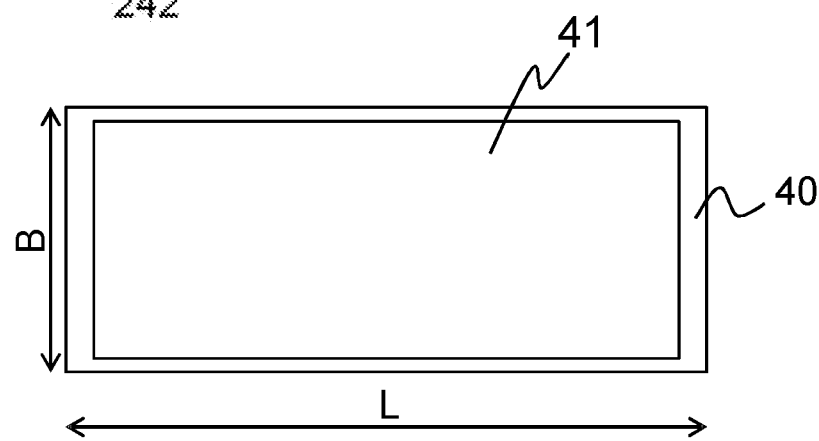
FIG. 15 schematically shows the piezoelement of FIG. 14 in a view from below, according to one or more embodiments of the invention.
Figure 16:
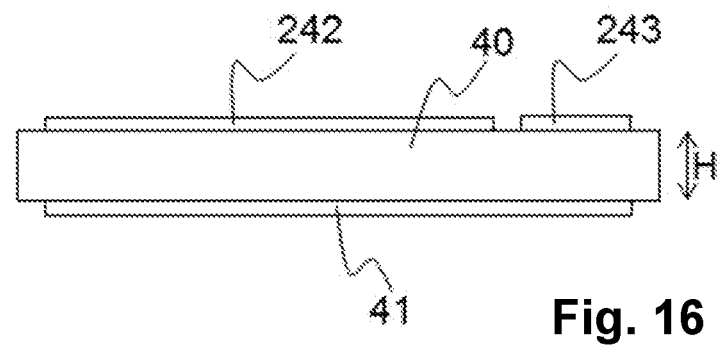
FIG. 16 schematically shows the piezoelement of FIG. 14 in a view from the shorter side, according to one or more embodiments of the invention.

By way of one or more embodiments, the piezoelement 11 as shown in FIGS. 14 to 16 differs from the piezoelement 11 as shown in FIGS. 10 to 12, in terms of the structure of the second electrode 242 and third electrode 243 arranged on the upper side of the piezoelectric layer 40. In at least one embodiment, the electrodes 242, 243 may include ribs arranged in a comb-like manner, wherein each rib of the second electrode 242 is arranged in a gap between two ribs of the third electrode 243, and vice versa. By way of one or more embodiments, a single electrode 41 may be provided on the underside of the piezoelectric layer 40, as shown in FIG. 15. In at least one embodiment, the second electrode 242 and the third electrode 243 may be galvanically separated from one another.

Figure 9:
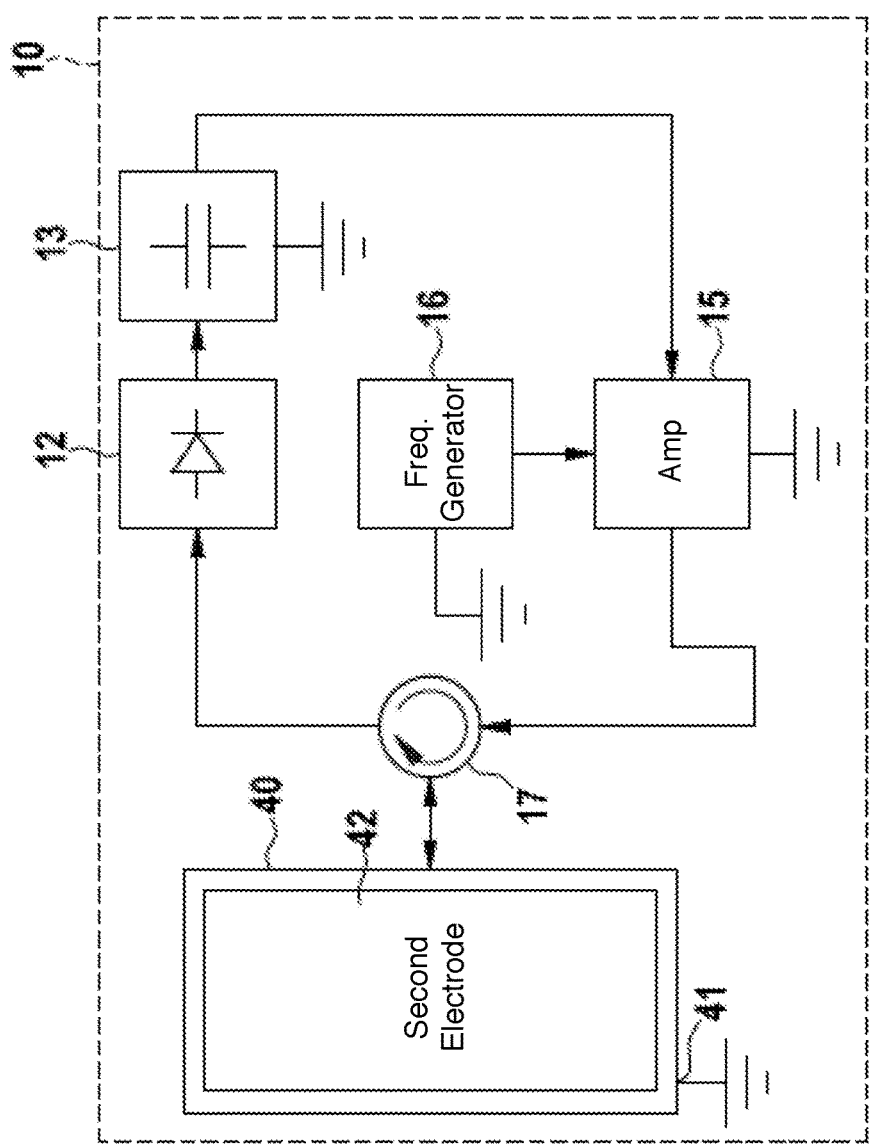
FIG. 9 schematically shows a first exemplary embodiment of the implant with the piezoelement of FIGS. 6 to 8 in a block diagram, according to one or more embodiments of the invention.
Figure 13:
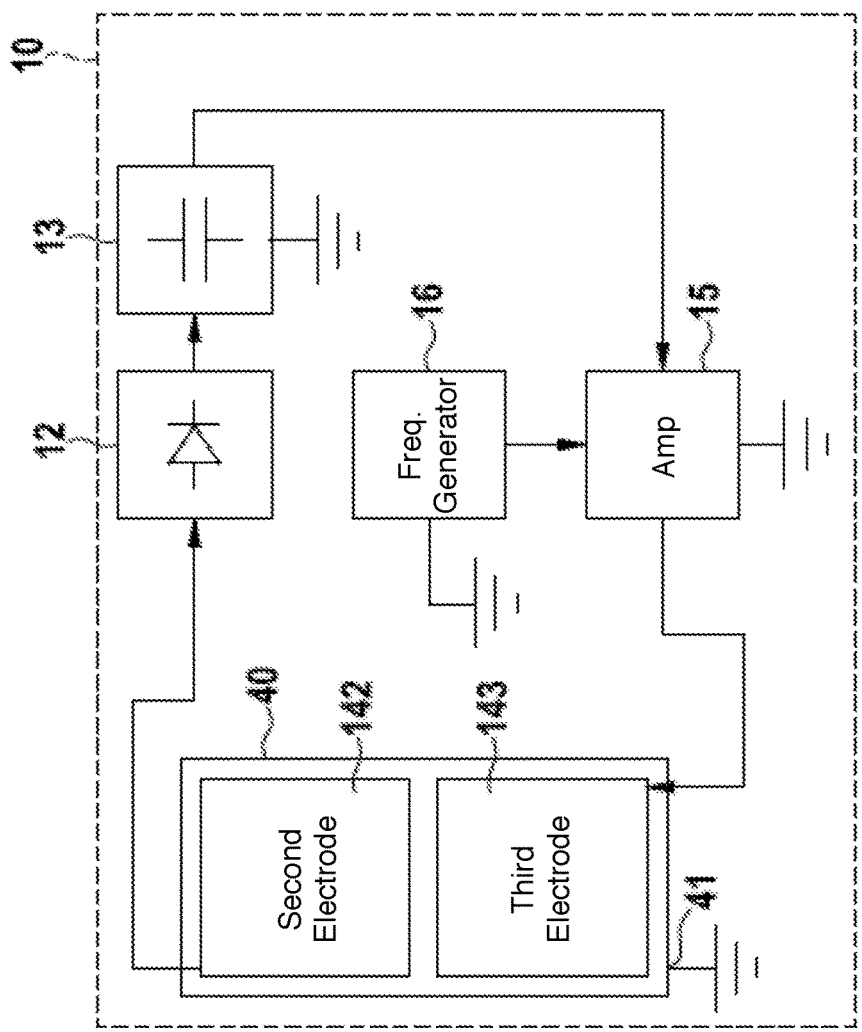
FIG. 13 schematically shows a second exemplary embodiment of the implant with the piezoelement of FIGS. 10 to 12 in a block diagram, according to one or more embodiments of the invention.
Figure 17:
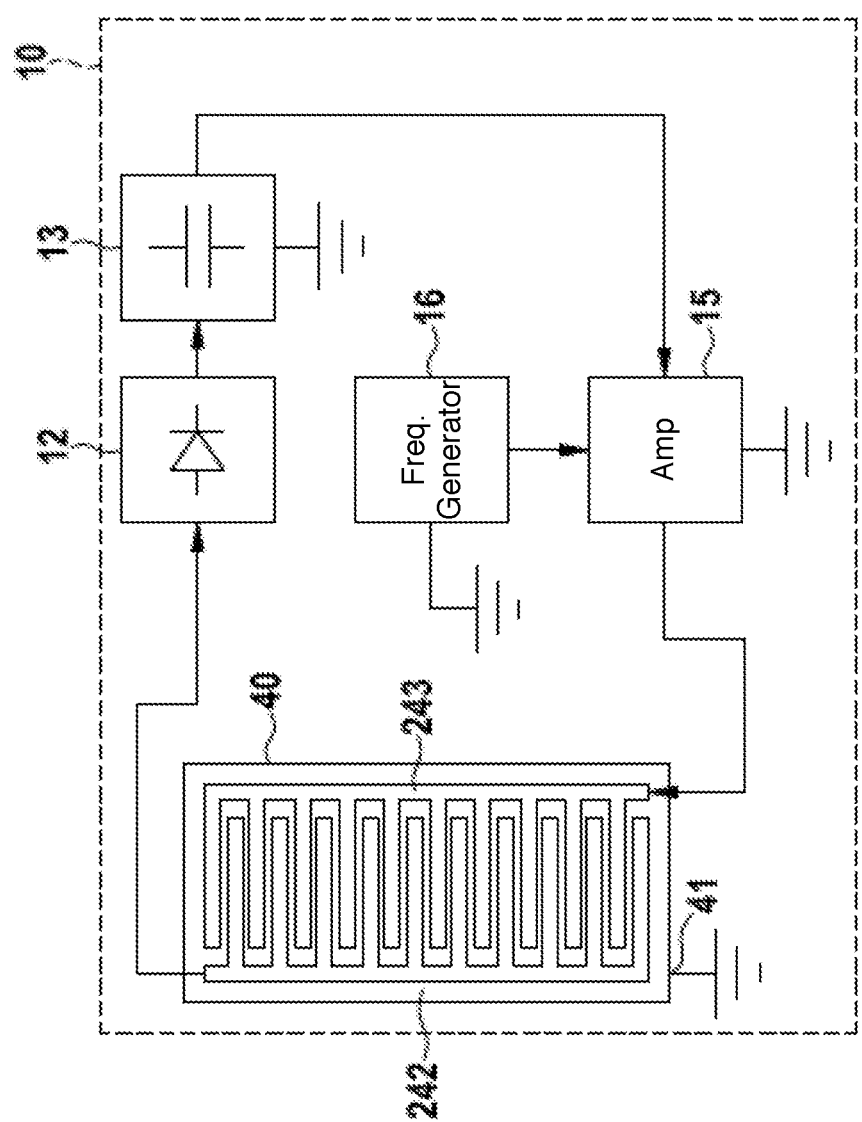
FIG. 17 schematically shows a third exemplary embodiment of the implant with the piezoelement of FIGS. 14 to 16 in a block diagram, according to one or more embodiments of the invention.

FIGS. 9, 13 and 17 show interconnection of the electrodes of the piezoelement 11, each as a block diagram, according to one or more embodiments of the invention. At least one embodiment may include two different circuit variants: a first circuit variant for a piezoelement 11 that includes two electrodes as shown in FIG. 9 and a second circuit variant for a piezoelement 11 that includes three electrodes as shown in FIGS. 13 and 17.

FIG. 9 shows the first circuit variant, according to one or more embodiments of the invention. In at least one embodiment, the first electrode 41 may be connected to ground, and the second electrode 42 may be connected to a circulator 17, wherein the circulator 17 separates the frequency $f_1$ of the incoming signal from the frequency $f_2$ of the outgoing signal. In one or more embodiments, the piezoelement 11 may receive a first ultrasound signal 21 having a frequency $f_1$, which may be converted into a corresponding incoming electrical signal having a frequency $f_1$. In at least one embodiment, the circulator 17 may forward the incoming signal having the frequency $f_1$ to a rectifier 12, such as a diode, and may then supply the incoming signal that is rectified to a capacitor 13, which may be or may include an intermediate energy store. In one or more embodiments, the incoming signal may be tapped at the capacitor 13. In at least one embodiment, the outgoing signal generated by the frequency generator 16, which may be amplified by the class E amplifier 15 and includes the frequency $f_2$, may be forwarded via another connection point of the circulator 17. According to one or more embodiments, the connection between the capacitor 13 and the class E amplifier 15 may serve as, may be or may include the energy supply of the amplifier. In at least one embodiment, the piezoelement 11 may convert the outgoing electrical signal into the second ultrasound signal 22. One or more embodiments may include a modulator (not shown), which modulates the outgoing signal via a frequency, amplitude, or phase modulation in order to transfer data from the implant 10 to the further apparatus.

According to at least one embodiment of the invention, FIG. 13 shows the interconnection of the electrodes 41, 142, and 143, and FIG. 17 shows the interconnection of the electrodes 41, 242, and 243 in accordance with the second circuit variant. In one or more embodiments, of FIGS. 13 and 17, the first electrode 41 may be connected to ground. In at least one embodiment, the second electrode 142, 242 may be connected to the rectifier 12, which rectifies an incoming electrical signal generated from the first ultrasound signal 21 with the frequency f1. In one or more embodiments, the rectified signal may then be supplied to a capacitor 13, which serves as, is or may include an energy store. In at least one embodiment, the incoming signal in the form of the frequency f1 may be tapped at the capacitor 13. In one or more embodiments, the third electrode 143, 243 in each case may be connected to the class E amplifier 15, may generate the second ultrasound signal 22 and may transmit the second ultrasound signal 22 with the frequency f2. In at least one embodiment, the frequency f2 may be provided electrically by the frequency generator 16 connected to the third electrode 143, 243 and may be amplified by the class E amplifier 15. In one or more embodiments, the connection between the capacitor 13 and the class E amplifier 15 may serve as, may be or may include the energy supply of the amplifier 15. In the second variant, at least one embodiment may include a modulator, which modulates the outgoing signal using one or more of a frequency, amplitude, and phase modulation in order to transfer data from the implant 10 to the further apparatus.

By way of one or more embodiments, the transmitting and receiving unit 30 of the further apparatus, for example a patient apparatus located outside of the body, may transmit a first ultrasound signal 21, for example at a frequency f1 of 320 kHz, using a transmitting/receiving sound converter 31. In at least one embodiment, the first ultrasound signal corresponds to the series resonance frequency of the piezoelement 11 of the implant 10 and is therefore received particularly efficiently by the piezoelement 11 and may be converted into a corresponding electrical AC voltage. In one or more embodiments, the electrical AC voltage may be rectified using a rectifier 12, which is connected to the piezoelement 11, and may be stored temporarily in a capacitor 13 connected to the rectifier 12. In at least one embodiment, the electrical energy in the form of a DC voltage stored in the capacitor 13 may be converted using a class E amplifier 15 and an oscillator 16 into an AC voltage having a frequency of 800 kHz. In one or more embodiments, the data ready to be transferred may be modulated using a modulator integrated into the class E amplifier 15 and may be converted via the piezoelement 11 at the second series resonance frequency f2 into a second ultrasound signal 22. According to at least one embodiment, the conversion of the electrical energy into mechanical energy is performed particularly efficiently by the piezoelement 11, since the conversion occurs at the second series resonance frequency f2. In one or more embodiments, the second ultrasound signal 22 may be received in the transmitting and receiving unit 30 of the further apparatus by via a transmitting/receiving sound converter 31, and may be rectified and demodulated. At least one embodiment may include high-pass filter 34, amplifier 34 and a demodulator 35 connected thereto to receive, rectify and demodulate the second ultrasound signal 22. In one or more embodiments, the transferred data may be extracted from the second ultrasound signal 22. At least one embodiment of the invention may include a memory (not illustrated) for the data transferred with the second ultrasound signal 22 and a processing unit (not illustrated) such as a microcontroller, µC, to process the data.

By way of one or more embodiments, the transmitting and receiving unit 30 of the further apparatus may be structured substantially similarly to the implant 10. In at least one embodiment, the transmitting and receiving unit 30 may include at least two sound converters provided in a sound converter unit 31: a first sound converter that generates and transmits the first ultrasound signal 21, and a second sound converter that receives and converts the second ultrasound signal 22. In at least one embodiment, the structure of the transmitting and receiving unit 30 of the further apparatus is therefore advantageous because the complexity of the signal processing is reduced by the separation of the processes of transmitting the first ultrasound signal 21 and receiving the second ultrasound signal 22 by at least two different sound converters.

In at least one embodiment of the invention, the transmitting and receiving unit 30 of the further apparatus, similarly to the implant 10, may be structured with a combined sound converter as shown in FIGS. 6 to 8, 10 to 12, and 14 to 16. In one or more embodiments, such a structure may be advantageous when the further apparatus is also an implant.

According to at least one embodiment, the implant 10 may be constructed in a space-saving manner, since the voltage source may be provided in a compact manner merely on account of the energy transferred with the ultrasound signal, such as during comprehensive communication. In one or more embodiments, the ultrasound signals used to transfer the data may include an extensive range, even in the body of a person. By way of at least one embodiment, the elements of the implant may be integrated in a metal housing, for example a metal housing that includes titanium.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE SIGNS 10 implant
11 piezoelement
12 rectifier
13 capacitor
15 class E amplifier
16 frequency generator
17 circulator
21 first ultrasound signal at a first frequency f1
22 second ultrasound signal at a second frequency f2
30 transmitting/receiving unit of the further apparatus
31 sound converter unit
32 frequency generator
33 high-pass filter
34 amplifier
35 demodulator
40 piezoelectric layer
41 first electrode
42, 142, 242 second electrode
143, 243 third electrode

What is claimed is:

1. An implant comprising:
   a receiver that receives first ultrasound signals emitted by a transmitting unit of a further apparatus,
   wherein said receiver comprises a piezoelement,
   wherein said piezoelement is excited by the first ultrasound signals at a first series resonance frequency (f1),
   wherein said piezoelement converts mechanical energy transferred with the first ultrasound signals into electrical energy,
   wherein said piezoelement is additionally excited at a second series resonance frequency (f2) using the electrical energy, wherein said second series resonance frequency (f2) differs from the first series resonance frequency (f1), and,
   wherein at the second series resonance frequency (f2), said piezoelement transmits second ultrasound signals.

2. The implant according to claim 1, wherein the piezoelement is excited at the first series resonance frequency (f1) and the second series resonance frequency (f2) simultaneously.

3. The implant according to claim 1, wherein the piezoelement comprises
   a thin rectangular piezoelectric layer,
   a height ranging from 100 μm to 1000 μm,
   side edges with lengths, wherein the lengths of the side edges determine the first and second series resonance frequencies (f1, f2).

4. The implant according to claim 3, further comprising
   a first electrode, wherein said thin rectangular piezoelectric layer comprises an underside, and wherein said first electrode is on the underside of said thin rectangular piezoelectric layer of the piezoelement; and,
   at least one second electrode, wherein said thin rectangular piezoelectric layer further comprises an upper side, and wherein said at least one second electrode is on the upper side of the thin rectangular piezoelectric layer of the piezoelement.

5. The implant according to claim 3, further comprising
   a first electrode, wherein said thin rectangular piezoelectric layer comprises an underside, and wherein said first electrode is on the underside of said thin rectangular piezoelectric layer of the piezoelement;
   a second electrode; and,
   at least one third electrode,
      wherein said at least one third electrode is galvanically separated from the second electrode,
      wherein said thin rectangular piezoelectric layer further comprises an upper side, and,
      wherein said second electrode and said at least one third electrode are arranged on the upper side of the thin rectangular piezoelectric layer.

6. The implant according to claim 5, wherein the second electrode and the at least one third electrode are arranged adjacently and form a rectangular layer on the upper side of the thin rectangular piezoelectric layer.

7. The implant according to claim 5, wherein the second electrode and the at least one third electrode on the upper side of the thin rectangular piezoelectric layer each comprise comb-like ribs, wherein the comb-like ribs of the second electrode and of the at least one third electrode engage with one another.

8. The implant according to claim 1, further comprising an amplifier,
   wherein the piezoelement is connected to said amplifier,
   wherein said amplifier generates an electrical output signal with the electrical energy that is converted at the first series resonance frequency (f1),
   wherein via said electrical output signal, the piezoelement is excited at the second series resonance frequency (f2) and generates the second ultrasound signals to be transmitted.

9. The implant according to claim 1, wherein a frequency distance between the first series resonance frequency (f1) and the second series resonance frequency (f2) is at least 100 kHz.

10. The implant according to claim 8, wherein the amplifier comprises a modulator, and wherein said modulator modulates the electrical output signal to cause a transfer of data.

11. A method for operating an implant comprising:
    providing an implant that comprises
       a receiver that receives first ultrasound signals emitted by a transmitting unit of a further apparatus, and wherein said receiver comprises a piezoelement,
    exciting the piezoelement by the first ultrasound signals at a first series resonance frequency (f1),
    converting mechanical energy transferred with the first ultrasound signals into electrical energy via said piezoelement,
    receiving the first ultrasound signals emitted by the transmitting unit via the piezoelement,
    exciting the piezoelement at a second series resonance frequency (f2) using the electrical energy,
       wherein said second series resonance frequency (f2) differs from the first series resonance frequency (f1), and,
    transmitting second ultrasound signals at the second series resonance frequency (f2) via the piezoelement.

12. The method according to claim 11, wherein said implant further comprises an amplifier, wherein said amplifier comprises a modulator, wherein the piezoelement is connected to said amplifier, and further comprising
    generating an electrical output signal with the electrical energy that is converted at the first series resonance frequency (f1) via the amplifier,
    exciting the piezoelement at the second series resonance frequency (f2) via said electrical output signal,
    generating the second ultrasound signals via the piezoelement, and,
    modulating the electrical output signal of the amplifier to cause a transfer of data.

* * * * *